United States Patent [19]
Horner et al.

[11] 3,959,107
[45] May 25, 1976

[54] COMBINATION ELECTRODE

[76] Inventors: Jack Edgar Horner, 1142 Santiago Drive, Newport Beach, Calif. 92660; Charles Richard Selby, 2801 N. Bristol St., No. 63, Santa Ana, Calif. 92706

[22] Filed: June 6, 1974

[21] Appl. No.: 477,076

[52] U.S. Cl. .................... 204/195 G; 204/195 F; 205/195 M
[51] Int. Cl.² ................. G01N 27/36; G01N 27/30
[58] Field of Search ............ 204/1 T, 195 G, 195 F, 204/195 M

[56] References Cited
UNITED STATES PATENTS

| | | | |
|---|---|---|---|
| 3,677,925 | 7/1972 | Tamate et al. | 204/195 G |
| 3,880,737 | 4/1975 | Brunt | 204/195 G |

*Primary Examiner*—T. Tung
*Attorney, Agent, or Firm*—Grover A. Frater

[57] ABSTRACT

An ion selective combination is formed by creating a measuring electrode from an elongated tube whose wall is made with a depression along its length. That wall depression is covered with a material of a kind that can be pierced by the needle of a syringe or otherwise treated so that an electrolyte, or a liquid to form an electrolyte, can be injected into the cavity formed by the depression and that covering material. The electrolyte in the cavity then serves as the electrolyte of a reference cell which is completed by some non-metallic means for conducting ions from the interior of the cavity to the exterior where contact is made with a material to be tested. That ion path can be completed by a salt bridge or by ionic conduction through the pliant or piercable cover over the cavity in which the electrolyte is housed. An electrode having those features is combined with a coaxial cable so that the electrode structure is formed on the end of the cable. Thus arranged, the cable serves as a tool for inserting and retracting the electrode into small openings and through catheters and the like.

15 Claims, 2 Drawing Figures

COMBINATION ELECTRODE

IMPROVEMENTS IN ION SELECTIVE ELECTRODES

This invention relates to improvements in the structure of ion selective electrodes.

While not limited thereto, the invention is particularly suited to the production of miniature ion selective electrodes and it is applicable to the production of electrodes in which the reference cell is arranged so that it need not be filled with electrolytic solution unitl the electrode is to be used.

An ion selective electrode is a device for detecting the presence of a particular kind of ion in a solution. It functions by measuring transfer or flow of that ion through a material that acts as a barrier to flow of any but that particular kind of ion. One structure that is commonly used in such electrodes employs a length of glass tubing, one end of which is sealed by a special glass which will allow conduction of hydrogen ions and is referred to as a "pH sensitive" glass. When a test solution contacts the outer surface of a pH sensitive seal (usually called a "membrane") whose inner surface is contacted by an electrolytic solution, then an electrical potential is developed across the seal or membrane. That potential may be measured accurately using two electrochemically identical half cells. The half cell is formed by a silver-silver chloride electrode immersed in electrolytic solution. In most cases, the electrolytic solution comprises a standard pH buffer solution and salt. A more general description is that the electrolyte is a saturated aqueous salt solution. It may contain an excess of salt. The half cell is formed by immersing into the electrolyte a silver wire which is partially coated with silver chloride. An alternative form places the silver in direct physical and electrical contact with an inner surface of the seal or membrane.

The potential developed across the seal or membrane is commonly applied across a variable resistive element - a potentiometer and a voltmeter measures the voltage drop across the potentiometer. The magnitude of the voltage is a measure of the acidity of the solution being tested.

The complete electrochemical circuit is described as follows. One terminal of the potentiometer is connected to a silver wire whose other end is partially coated with silver chloride. That end of the wire is immersed in a body of electrolytic solution. The electrolytic solution is contained in a vessel of insulating material such, for example, as a glass tube which can be partly immersed in the test solution. A means is provided in the wall of the tube for transferring ions between the electrolytic solution and the test solution. That means may comprise a liquid junction sometimes called a salt bridge. It is an electrolyte filled passage of minute dimensions from the interior of the tube to its exterior at a point where it will contact the test liquid. Instead of a liquid junction, the connection between electrolyte and test solution may be made through a membrane of a material which transfers ions without measurable potential drop. Such materials are described as hydrophilic, semi-permeable and hydrophobic, salt dispersed.

Thus far described, the circuit extends from one side of the potentiometer to the test solution. The only potential is the one at the interface of the silver-silver chloride and electrolyte. It is called the reference potential and the tube, half cell and liquid junction are called the reference electrode or reference cell.

The other side of the potentiometer is connected to another silver wire which has its end partially coated with silver-silver chloride and immersed in a second body of electrolyte housed in a second glass tube. The ion selective seal, in this example, the pH sensitive glass, is formed in the wall of the second tube. The combination of the second silver-silver chloride and electrolyte half cell, second tube and ion selective seal is called the measuring cell or measuring electrode. When it is immersed in the test solution, two potentials are developed. One is developed at the silver-silver chloride electrolyte interface or half cell. It is equal to the potential developed in the reference cell. The other potential is the one across the pH glass membrane. Its magnitude is a measure of test solution acidity.

When both the reference and measuring electrodes are placed in the test solution, the circuit can be traced from potentiometer to the reference half cell (silver to electrolyte) to test solution to pH membrane to measuring half cell (electrolyte to silver) and back to the potentiometer. The potentials across the two half cells are connected in opposition. They are cancelled. Only the potential across the pH membrane appears across the potentiometer.

A number of factors tend to complicate efforts to design and produce such ion selective electrodes. Some of those factors are important here. First, it is often desirable or necessary to combine the reference cell and the measuring cell into a composite structure, referred to as a "combination electrode". Second, the electrolytes are usually aqueous solutions that are saturated with salt. If there is any evaporation, salt crystals are formed which can interfere with proper operation of the electrode and contaminate the test solution. A third factor is the requirement that electrical contact with the test sample be made with the electrolyte at the reference cell side of the combination electrode without development of a measurable potential or potential drop.

These several factors pose sufficiently difficult design and production problems so that it has been very difficult prior to this invention to make a miniature combination electrode. It has been very difficult, prior to this invention, to produce a combination electrode at a sufficiently low cost so that it could be treated as a disposable unit. The invention overcomes these difficulties. It is not possible to produce a highly accurate, miniaturized combination electrode at a price sufficiently low so that it can be considered a throw-away item, even in the economy of the underdeveloped nations. Moreover, the invention makes it possible to produce a combination electrode which may be shipped with the electrolyte for its reference cell in dry form, thus to provide very long storage life and to eliminate other problems such as the loss of electrolyte during high altitude air shipments.

The third problem factor mentioned above was the requirement that the test solution be brought into electrochemical contact with the internal electrolyte of the reference celll without developing interfering potentials or potential drops.

That can be done in either of two ways. The most common way is to arrange a fluid path from the interior of the container that holds the reference cell electrolyte to the exterior of that container where the end of the path can be immersed in the test material. Such immersion completes a liquid path called a "liquid junction" reference cell electrolyte to the test material. When the electrode is not immersed in the test material that "liquid junction" constitutes a leak.

The alternative is to form part of the wall of the reference cell container of a material through which the electrolyte solution cannot pass to mix with the test solution, but through which ionic conduction is possible. There are two classes of such material. Both permit the flow of ions and both tend to greatly limit the passage of liquid. One class of material is described as hydrophilic and semi-permeable. Usually, it is necessary to form material of that class into thin membranes. Examples of such materials include cellulose acetate and the materials that bear the trademarks Cellophane and Colloidan. The other class of materials combines hydrophobic polymers with salt particles that are distributed throughout the polymer. The salt is taken from the group consisting of potassium chloride, sodium chloride and potassium nitrate. While the use of such ion permeable, flow inhibiting materials sounds attractive, those materials have their limitations and are suitable for use only in certain kinds of test solutions.

SUMMARY OF THE INVENTION

The invention provides a novel arrangement for adding a reference cell to the exterior of an ion selective measuring cell. The latter is formed of an elongated container, one end of which is fitted with a seal that is selective to the ion to be measured. The outer wall of that container is depressed and the wall around the depression is covered with a material which is elastomeric, or at least pliant, and through which a hypodermic needle can be inserted. That covering over the depression forms a cavity. The electrolyte of the reference cell is disposed within that cavity. It is explained above that the contact between the reference cell electrolyte and the test material may be made either through a convention liquid junction or through an ion-permeable membrane. In any event, it is made through "a non-metallic means for conducting ions between the exterior of the combination electrode and said cavity". Whether the liquid junction or the ion permeable membrane be used, it is possible to manufacture the unit so that the electrolyte in that cavity, the electrolyte of the reference cell, is in liquid form. However, in the preferred form of the invention, whether the "non-metallic means for conducting ions" is a liquid junction or an ion-permeable membrane, the electrolyte is dry, constituting dried salts with or without a binder or buffer materials. When the electrode is to be made active, it is only necessary to inject a small quantity of distilled water or saline solution into the cavity through the pliant, or elastomeric, covering. That water will promptly wet the salt in the cavity and in the liquid junction, if there is a liquid junction, so that the combination cell is rendered fully operative within moments after injection of water.

The preferred construction includes a number of other features, among them an arrangement in which conductor leads to the unit are housed in a coaxial cable one end of which is inserted into the measuring cell container where it cooperates with several bodies of sealing compound to seal the electrolyte in that measuring cel. Another feature is the use of heat shrinkable tubing to fasten the cell container and coaxial cable in place relative to one another. Another feature is the combined use of both classes of ion permeable material in making the pliant covering member that with the depression in the measuring cell container forms a cavity for the electrolyte of the reference cell. These and other features of the invention will become apparent and more easily understood in the detailed description below of two embodiments of the invention.

Figure 2:
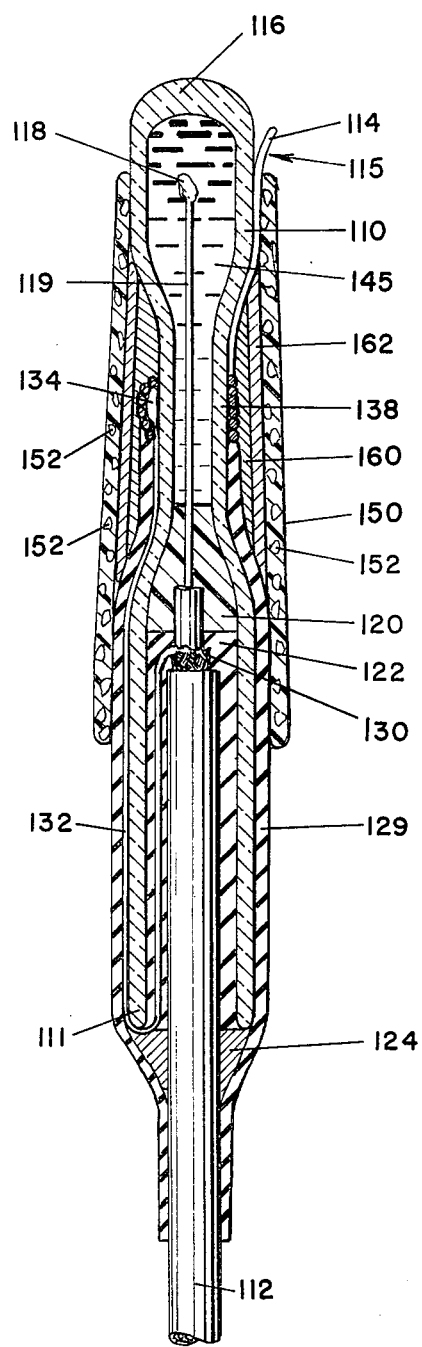
FIG. 2 is a cross-sectional view of an alternative form of combination electrode shown with a section, less than the whole, of its measuring lead cable.

The combination electrodes shown in the drawings are greatly enlarged. In practice, the outside diameter of both of these units is less than 345 millimeters. The overall length of the central tube 10 in FIG. 1, and the central tube 110 in FIG. 2, is approximately 2.7 centimeters.

Figure 1:
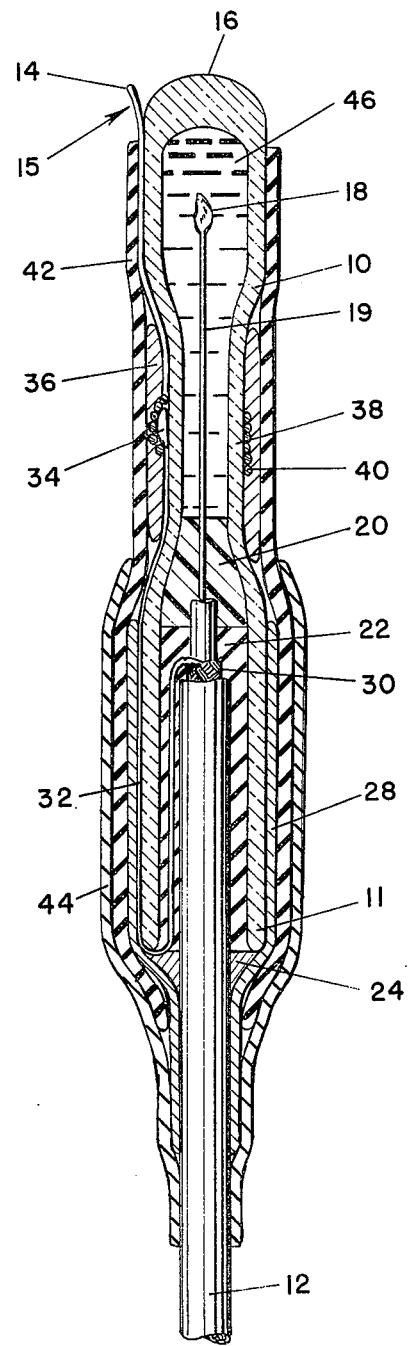
FIG. 1 is a cross-sectional view of a combination electrode, made according to the invention, only a portion of its coaxial lead cable being shown.

The connecting lead in both embodiments is a coaxial cable which extends axially from one end of the measuring electrode. At least that part of the coaxial cable that is disposed within the central tube is considered to be part of the combination electrode in these embodiments. The coaxial cable in the case of FIG. 1 is designated 12, and in the case of FIG. 2 it is designated 112. While the cables bend relatively easily, they have sufficient compressive strength so that these electrodes may be threaded through a small catheter simply by pushing on the coaxial cable at a point near the entrance to the catheter. Upon emerging from the catheter, the end of the electrode, the upper end in FIGS. 1 and 2, engages body fluids. The ends 14 and 114 of threads 15 and 115, respectively, are laden with salts and, if not previously wetted, are wetted by the body fluids so that both the thread and the surface of ph sensitive glass at the end of the electrode mades electrical contact with the fluids. Ultimately, the thread end 15 pH the surface of pH sensitive glass 16, in the case of FIG. 1, are connected to the shield and center conductor, respectively, of the coaxial cable 12. Using appropriate instrumentation, not shown in the drawings, the potential between the inner and outer conductors to the cable is measured and the magnitude of that potential is a measure of the pH of the body fluid.

Referring first to FIG. 1, this structure includes two electrodes. One of those electrodes is formed by the tube 10, the upper end of which is sealed closed by an ion selective membrane. In this case, the membrane is formed of glass and it is hydrogen-ion selective so that the current flowing through it and the potential across it are a measure of pH of the substance that contacts its outer surface. The tube 10 must be made of an insulating material. Ordinarily, as in this case, it is made of glass. The center conductor of coaxial cable 12 must be placed in electrical contact with the inner surface of the membrane 16. In this case, that center conductor has been stripped of insulation and silvered. A small quantity, or lump, 18, of silver chloride mixture has been deposited electrolytically or thermally on the end of silver wire 19.

The upper end of the tube 10 is filled with an electrolyte in which the silver wire 19 and the silver-silver chloride end 18 are immersed. The electrolyte is sealed in place permanently by plugs 20 and 22 of electrically non-conducting, polymeric material. the coaxial cable extends into the tube 10 for about one-third the length of the tube. The inner diameter of the tube is only slightly larger than the outer diameter of the coaxial cable, and the space between them is filled by the material of plug 22 at the forward end and by a quantity 24 of silastic rubber in the region of the rearward end 11 of tube 10. That construction fixes the electrode firmly to the end of the coaxial cable and assures that the electrode and the cable end extend on substantially the same axis. In this embodiment, that inner connection between coaxial cable and electrode is made even stronger by the use of a sleeve 28 of heat-shrinkable, insulating material. When first assembled on the electrode, it comprises a tube of uniform diameter and it is placed on the electrode such that it encompasses the rearward one-third or so of the tube 10, and so that the other part of its length encompasses the coaxial cable 12 at the rear of the tube. The sleeve is then heated so that it shrinks into tight engagement with the tube 10 and the coaxial cable 12 and the silastic material 24.

The heat-shrinkable sleeve, or sheath, serves another purpose. A wire 32 is connected to the outer braid or shield of the cable at a point 30 where the outer jacket of the coaxial cable ends. That wire, 32, extends back through the tube 10 between the jacket of the coaxial cable and the inner wall of the tube. At the point where it emerges from the end 11 of the tube, wire 32 is bent forwardly along the outer surface of the tube between the outer wall of the tube 10 and the inner wall of the sleeve, or sheath, 28. The sleeve 28 holds the wire in that position.

The wire 32 is connected to a half cell that forms part of the reference electrode. At least the end of the wire 32 is silver and is coated with a quantity, or lump, 34 of silver chloride material. The reference cell also includes an electrolyte, some means for retaining the electrolyte in close proximity to the ion selective electrode, and it includes some non-metallic means for conducting ions from the body of the electrolyte to the exterior of the electrode structure where those ions can flow to a test material. In the invention, a reservoir for that electrolyte is created by forming a depression in the surface of the tube 10 in this example, that houses and forms a part of the measuring electrode. That depression is then covered with a material, here called a "pliant member" for convenience, which can be pierced to permit the injection of electrolyte or of water which will form an electrolyte with salts that are already contained in that depression. The "pliant member" covers the depression so that the depression is converted to a closed cavity for electrolyte material in wet or in dry form. In this connection, the term "dry electrolyte" means a salt which can be converted to an electrolyte by the addition of a liquid, usually water.

In the preferred embodiment, the depression and cavity is formed by reducing the diameter of the measuring electrode tube at a point along its length. The reduction extends over about a third of the length of the tube in the region of a third or a half of the distance from the front end of the tube. That depression, or annular reduction in diameter, may be formed in an early stage of construction by heating the glass tube until the glass in the region of the depression is soft and then forming a section of reduced diameter by stretching the tube or by pressing inward upon its outer surface. The inside diameter must not be made so small that the forward end of the tube cannot be filled with electrolyte or so small that the silver wire 19 and the silver chloride end may not be inserted into the electrolyte. On the other hand, the reduction in diameter should be sufficient to form an outer, annular space in which the end of silver wire 32 and the silver chloride end 34 may be disposed together with a quantity 36 of dried salt and a few thread wrappings.

The reference cell is completed after the sleeve, or sheath, 28 is assembled over the measuring electrode and the forwardly extending length of wire 32. The end of the wire and its glob of silver chloride material 34 is placed in the depression in the wall of the tube 10. If the wire 32 is longer than needed, it is simply wrapped around neck portion 38 of tube 10. In this embodiment, the liquid junction is formed by the thread 15. The thread may be composed of any material that will wet and which will contain and retain salt when the liquid of the electrolyte has evaporated away. Cotton thread makes a good liquid junction. The thread is soaked in a saturated solution of salt. A few turns of that thread are taken around the neck 38 and the end of wire 32 so that both the wire and the thread are retained in place. Some of the turns of the thread are visible in FIG. 1 where some of them are identified as the reference numeral 40. An end of the thread is made to extend forwardly alongside the tube 10. The end of wire 32 and the silver-silver chloride glob 34 and the turns 40 of the thread are then coated with a material that contains salt. That can be accomplished by painting on an electrolyte solution and permitting the liquid constituent to evaporate so that only a crust of salt remains. A more convenient arrangement is to mix that salt with a small quantity of polymer of the kind that foams into an open cellular structure so that a mass is formed which, when wetted, will serve as an electrolyte in electrical contact with the salt in the thread and the silver-silver chloride 34.

Thus, the ring of material 36 includes a salt which, when wetted, will make electrical contact both with the silver-silver chloride and the thread 15. When that layer 36 is dried, it is covered with the "pliant element". In this case, that element is an elastomeric material, more specifically, a synthetic rubber sleeve. The sleeve is drawn over tube 10 and thread 15 and the materials 34 and 36 and the shrunken sleeve 28. The size of the rubber sleeve 42 is such that it elastically grips tube 10 in the region forward of the necked down portion 38 and so that it elastically grips the shrink tube 28 whereby a sealed container is formed.

The thread 15 must extend forwardly between the rubber sleeve 42 and the tube 10 and it must emerge from that space to the exterior of the unit as end 14 is shown to do. In this embodiment, the rubber sleeve is fixed in place by a second, outer, length of heat-shrinkable tubing 44 which is shrunk over the rear portion of the combination electrode and the length of the coaxial cable 12.

The body of electrolyte 46 in which the silver wire 19 and silver chloride end 18, are immersed, is formed of standard pH buffer solution with KCl present. The salt, potassium nitrate or the salt, sodium chloride could have been used instead.

If the inner walll of the tube 10 and the pH glass seal are coated with silver, which interfaces with silver chloride, the electrolyte and the silver chloride glob 18 could be ommitted. In that case, the wire 19 would be electrically connected to that silver coating. While that alternative is available, the construction shown is preferred.

The salt in the body 36 can be made of sodium chloride, potassium chloride or potassium nitrate. The invention does not depend upon the use of any particular one of those salts, nor is it limited to use of those salts.

To activate the combination electrode shown in FIG. 1, it is necessary only to inject water into the cavity between neck 38 of tube 10 and the inner wall of the rubber sleeve 42. The rubber wall is easily pierced with a needle of a hypodermic syringe. In the preferred construction, element 42 is not stretched so much that the puncture hole is pulled open after the needle is withdrawn. On the other hand, one of the advantages of the invention is that the unit is operative whether or not that puncture remains open or closes. It is necessary to complete a path for ions from the interior of the cavity, and it ordinarily makes little difference whether that be done through a puncture in the wall of the rubber sleeve or whether the ion path is completed by wetting and dissolving the salts in the thread 15.

Because the unit is arranged so that its electrolyte salts can be wetted at the time and at the place where the electrode is to be used, it is possible to store it for protracted periods. It will be apparent that the unit can be shipped by air because the reduction of ambient pressure that is experienced in air transport will have no deleterious effect. It will also be apparent that it makes no difference ultimately whether the quantity 36 of salt is wet or dry when the unit is first manufactured. It makes no difference ultimately whether or not that salt is dried during manufacture or after manufacture and it makes no difference if it never dries. Those questions are made moot by the injection of liquid at the time that the electrode is to be used.

The embodiment in FIG. 2 is like the embodiment in FIG. 1 except in its reference cell construction. The tube 110 is like tube 10 of FIG. 1. It is sealed at its upper end by a "membrane" 116 of pH sensitive glass. A quantity of electrolyte 145 is housed in the upper end of the tube 110. A silver coated wire 119 having a silver chloride glob 118 solidified on its end is immersed in the electrolyte. The wire 119 is the end of the center conductor of a length of coaxial cable 112. The electrolyte is sealed in place by a plug 120 that corresponds to plug 20 in FIG. 1. In FIG. 2, the seal is doubled as it is in FIG. 1 by a second plug 122 which corresponds to plug 22. The coaxial cable 112 extends into the lower portion of the tube 110 in the manner described in connection with FIG. 1. The outer jacket ends at a point about one-third of the way into the tube to expose the outer shield 130 of the coaxial cable 112. A conductor 132 is connected to that outer shield and it extends rearwardly between the jacket of the coaxial cable and the inner wall of the tube 110 to the rearward end 111 at which point the wire is bent forwardly so that it lies along the outer surface of the tube. It extends to that region 138 where the tube is necked-down to smaller diameter in the manner of region 38 of tube 10. At its end, the silver wire 132 is coated with a quantity or glob 134 of silver chloride material. A quantity 124 of silastic rubber is used to close the end of the tube at the point where the coaxial cable 112 emerges from it.

Except for small manufacturing differences, the construction of the unit shown in FIG. 2, thus far described, is like the construction shown in FIG. 1.

The unit of FIG. 2 includes a sheath of plastic material of the kind that shrinks when heated. The sheath 129 has been shrunk so that part of it embraces the tube 110 and so that part of it embraces the silastic rubber material 124 and the coaxial cable 112. It is similar to sheath 28 in FIG. 1 except that it extends forwardly in greater degree so that it surrounds part of the necked-down portion 138 of tube 110. Having reduced diameter at both ends, it will be prevented from a longitudinal movement relative to the tube, and, because of the gripping action of the silastic rubber 124, it will prevent relative movement between the tube and coaxial cable 112.

Instead of a rubber sheath like the sheath 42 of FIG. 1, the indentation in the wall of tube 110 is converted to a cavity by a sleeve 150 of a material which is inhibitory to liquid flow but which transmits ions with sufficient ease so that it can serve as a substitute for a more conventional liquid junction. The sleeve 150 is formed of a hydrophobic polymer which contains grains of salt in sufficient quantity so that ion transfer can proceed through the sleeve via those salt grains. The grains are visible in the cross-sectional view of FIG. 1 where a number of them are identified by the reference numeral 152. The salt granules are taken from the group which consists of potassium chloride, sodium chloride, and potassium nitrate.

In FIG. 2, a salt bridge is provided by a thread 115 whose end extends to the exterior of the electrode passing from the cavity between the exterior of tube 110 and the interior surface of the sleeve 150. The other end of that thread is wound around the neck 128 of the tube and, in the preferred embodiment, it is wound around the wire 132 and glob 134 so that they are held in position against the neck 38.

In this embodiment, the electrolyte is wet. It is identified by the reference numeral 160. In this case, the electrolyte includes all three of the salts, potassium nitrate, potassium chloride, and sodium chloride. The liquid electrolyte is held in place by a special, inner sleeve 162. That sleeve also serves as a "pliant element" which overlies the "depression" in tube 110 to form the electrolyte cavity. In this case, the sleeve 162 is assembled on the tube 110 and then the cavity is filled with electrolyte from the end of the sleeve rather than by piercing the sleeve. The sleeve 162 is made of one of the materials that inhibits liquid flow but which will allow ionic conduction from the electrolyte to the test solution, in this case through the outer sleeve 150 which also inhibits liquid flow, but which will allow ionic conduction. In this embodiment, sleeve 162 is made of vinyl acetate.

The unit of FIG. 2 includes a liquid junction in the form of thread 115. If the test solution is not contacted by that thread, proper operation is still possible by conduction of ions through sleeve 162 and 150. The vinyl acetate sleeve 162 would be entirely adequate, except that it is readily damaged. Its integrity is protected by the outer sleeve 150 and the unit will operate properly even though layer 150 is damaged. In fact, the unit will operate properly if both of the sleeves 150 and 162 are pierced because liquid flowing from the opening simply operates as a second liquid junction. Of course, if both layers are pierced, then the electrolyte 160 may become dry. In that case, it only requires an injection of a small quantity of water using a hypodermic syringe to reactivate the cell in the manner in which the unit in FIG. 1 is activated.

Although we have shown and described certain specific embodiments of our invention, we are fully aware that many modifications thereof are possible. Our invention, therefore, is not to be restricted except insofar as is necessitated by the prior art.

We claim:

1. In a combination, ion sensitive and reference electrode:
 an elongated electrically non-conducting tube, one end of which is fitted with a specific ion permeable seal;
 first connection means within said tube for making electrochemical connection to the inner side of said seal;
 said tube being formed with a depression in its exterior surface;
 means for creating a cavity of the space overlying said depression which can be entered from the exterior of the electrode by a needle comprising a pliant member formed of a substance that may be pierced with a needle from the exterior of the electrode, and carried by said tube and overlying said depression such that said depression forms a cavity between said pliant member and said tube and exposed at the exterior of said electrode;
 second connection means comprising a metallic electrical conductor terminating in said cavity;
 non-metallic means for conducting ions between the exterior of said combination electrode and said cavity; and
 a quantity of salt other than a salt of the metal of said metallic electrical conductor in said cavity in physical contact with said second connection means and with said non-metallic means.

2. The invention defined in claim 1 in which said salt is taken from the group consisting of potassium chloride, sodium chloride, and potassium nitrate.

3. The invention defined in claim 2 in which said permeable seal is formed of pH sensitive glass.

4. The invention defined in claim 3 in which said tube is formed of glass.

5. The invention defined in claim 4 in which said depression is formed by an annular, necked down, reduction in the outer diameter of the tube.

6. The invention defined in claim 2 in which said pliant member comprises a layer of elastomeric material capable of being pierced by the needle of a syringe.

7. The invention defined in claim 1 in which said non-metallic means for conducting ions comprises either a hydrophilic, semi-permeable membrane material or a hydrophobic polymer having particles distributed therethrough of a salt taken from the group consisting of potassium chloride, sodium chloride and potassium nitrate.

8. The invention defined in claim 7 in which said non-metallic means for conducting ions comprises a hydrophilic, semi-permeable membrane material.

9. The invention defined in claim 7 in which said non-metallic means for conducting ions comprises a hydrophobic polymer having particles distributed therethrough of a salt taken from the group consisting of potassium chloride, sodium chloride and potassium nitrate.

10. The invention defined in claim 9 in which said seal is a quantity of pH sensitive glass.

11. In a combination, ion sensitive and reference electrode:
 an elongated electrically non-conducting tube, one end of which is fitted with a specific ion permeable seal;
 first connection means within said tube for making electrochemical connection to the inner side of said seal;
 said tube being formed with a depression in its exterior surface;
 means for creating a cavity of the space overlying said depression which can be entered from the exterior of the electrode by a needle comprising a pliant member formed of a substance that may be pierced with a needle from the exterior of the electrode, and carried by said tube and overlying said depression such that said depression forms a cavity between said pliant member and said tube and exposed at the exterior of said electrode;
 second connection means comprising a metallic electrical conductor terminating in said cavity;
 non-metallic means for conducting ions between the exterior of said combination electrode and said cavity;
 a coaxial cable the center conductor of which comprises said first connection means and the outer conductor of which comprises said second connection means, a length of said cable being disposed in the other end of said tube;
 said second connection means extending from within said tube along said cable to said other end of the tube and then along the exterior of the tube to said depression;
 means in the form of a heat shrinkable plastic tube embracing a portion of the length of the tube and the cable extending therefrom for fastening the cable to the tube and retaining said second connection means in place; and
 said non-metallic means for conducting ions between the exterior of said electrode to the interior comprising a quantity of salt other than a salt of the metal of said metallic electrical conductor in said cavity in contact with said second connection means and a liquid junction extending from said quantity of salt to the exterior of the electrode.

12. The invention defined in claim 11 in which said pliant member comprises a sleeve of elastomeric material embracing areas of the tube around said cavity such that liquid injected through an injection opening into said cavity through said elastomeric material is retained in said cavity other than at said salt bridge and at said injection opening.

13. The invention defined in claim 12 in which said liquid junction comprises a salt filled thread.

14. The invention defined in claim 13 in which said depression is formed as section of said tube intermediate its ends being necked-down to a diameter less than that of the remainder of the tube.

15. The invention defined in claim 13 in which said first and said second connection means both terminate in a quantity of silver and silver chloride;
 said salt being taken from the group consisting of potassium nitrate, potassium chloride and sodium chloride; and
 said first connection means further comprising a saturated solution of said salt.

* * * * *